(12) United States Patent
Venturelli et al.

(10) Patent No.: US 8,870,940 B2
(45) Date of Patent: Oct. 28, 2014

(54) ENDOLUMENAL PROSTHESIS

(75) Inventors: Andrea Venturelli, Concesio (IT); Silvio Schaffner, Berlingen (CH)

(73) Assignee: Medtronic, Inc., Minneapolis, MN (US)

( * ) Notice: Subject to any disclaimer, the term of this patent is extended or adjusted under 35 U.S.C. 154(b) by 1587 days.

(21) Appl. No.: 11/996,378

(22) PCT Filed: Jul. 25, 2005

(86) PCT No.: PCT/IT2005/000436
§ 371 (c)(1),
(2), (4) Date: Jan. 22, 2008

(87) PCT Pub. No.: WO2007/013102
PCT Pub. Date: Feb. 1, 2007

(65) Prior Publication Data
US 2008/0215129 A1 Sep. 4, 2008

(51) Int. Cl.
*A61F 2/06* (2013.01)
*A61F 2/91* (2013.01)
*A61F 2/915* (2013.01)
*A61F 2/89* (2013.01)
*A61F 2/95* (2013.01)
*A61F 2/966* (2013.01)
*A61F 2/82* (2013.01)

(52) U.S. Cl.
CPC . *A61F 2/91* (2013.01); *A61F 2/915* (2013.01); *A61F 2/89* (2013.01); *A61F 2/95* (2013.01); *A61F 2/966* (2013.01); *A61F 2002/825* (2013.01); *A61F 2002/828* (2013.01); *A61F 2002/9155* (2013.01); *A61F 2210/0004* (2013.01); *A61F 2250/0031* (2013.01); *A61F 2250/0071* (2013.01)
USPC ........................................................ 623/1.15

(58) Field of Classification Search
USPC ............... 623/1.1, 1.11, 1.15–1.17, 1.19, 1.2, 623/1.23
See application file for complete search history.

(56) References Cited

U.S. PATENT DOCUMENTS

| | | | | |
|---|---|---|---|---|
| 5,306,286 A | * | 4/1994 | Stack et al. | 623/1.12 |
| 5,824,040 A | * | 10/1998 | Cox et al. | 623/1.35 |
| 6,165,214 A | * | 12/2000 | Lazarus | 623/1.35 |
| 6,258,117 B1 | * | 7/2001 | Camrud et al. | 623/1.16 |
| 6,540,777 B2 | * | 4/2003 | Stenzel | 623/1.16 |
| 6,565,599 B1 | * | 5/2003 | Hong et al. | 623/1.15 |
| 6,805,705 B2 | * | 10/2004 | Hong et al. | 623/1.15 |
| 7,323,008 B2 | * | 1/2008 | Kantor et al. | 623/1.15 |
| 7,329,276 B2 | * | 2/2008 | Smith et al. | 623/1.16 |
| 7,789,906 B2 | * | 9/2010 | Blank | 623/1.16 |
| 2002/0107563 A1 | | 8/2002 | Shanley | |
| 2002/0120327 A1 | * | 8/2002 | Cox et al. | 623/1.16 |
| 2002/0151964 A1 | * | 10/2002 | Smith et al. | 623/1.16 |
| 2003/0028245 A1 | * | 2/2003 | Barclay et al. | 623/1.22 |

(Continued)

FOREIGN PATENT DOCUMENTS

| | | |
|---|---|---|
| WO | 01/15751 | 3/2001 |
| WO | 03/015663 | 2/2003 |
| WO | 2004/045474 | 6/2004 |

*Primary Examiner* — Dianne Dornbusch

(57) ABSTRACT

The present invention relates to an endolumenal prosthesis comprising a tubular body adapted to convert from a contracted condition to an expanded condition. The tubular body develops along a longitudinal axis and comprises: a plurality of coils and at least one bridge. The coils develop along a substantially circumferential direction and the bridge connects two coils. The coils are realized in a persistent material, while the bridge is realized in a bioabsorbable material.

46 Claims, 17 Drawing Sheets

(56) References Cited

U.S. PATENT DOCUMENTS

| | | |
|---|---|---|
| 2004/0093077 A1 | 5/2004 | White et al. |
| 2004/0106975 A1* | 6/2004 | Solovay et al. .............. 623/1.11 |
| 2004/0106980 A1 | 6/2004 | Solovay et al. |
| 2004/0199242 A1* | 10/2004 | Hong et al. .................. 623/1.16 |
| 2005/0033399 A1* | 2/2005 | Richter ........................ 623/1.11 |
| 2005/0038501 A1* | 2/2005 | Moore et al. ................. 623/1.19 |
| 2006/0069424 A1* | 3/2006 | Acosta et al. ................ 623/1.12 |

\* cited by examiner

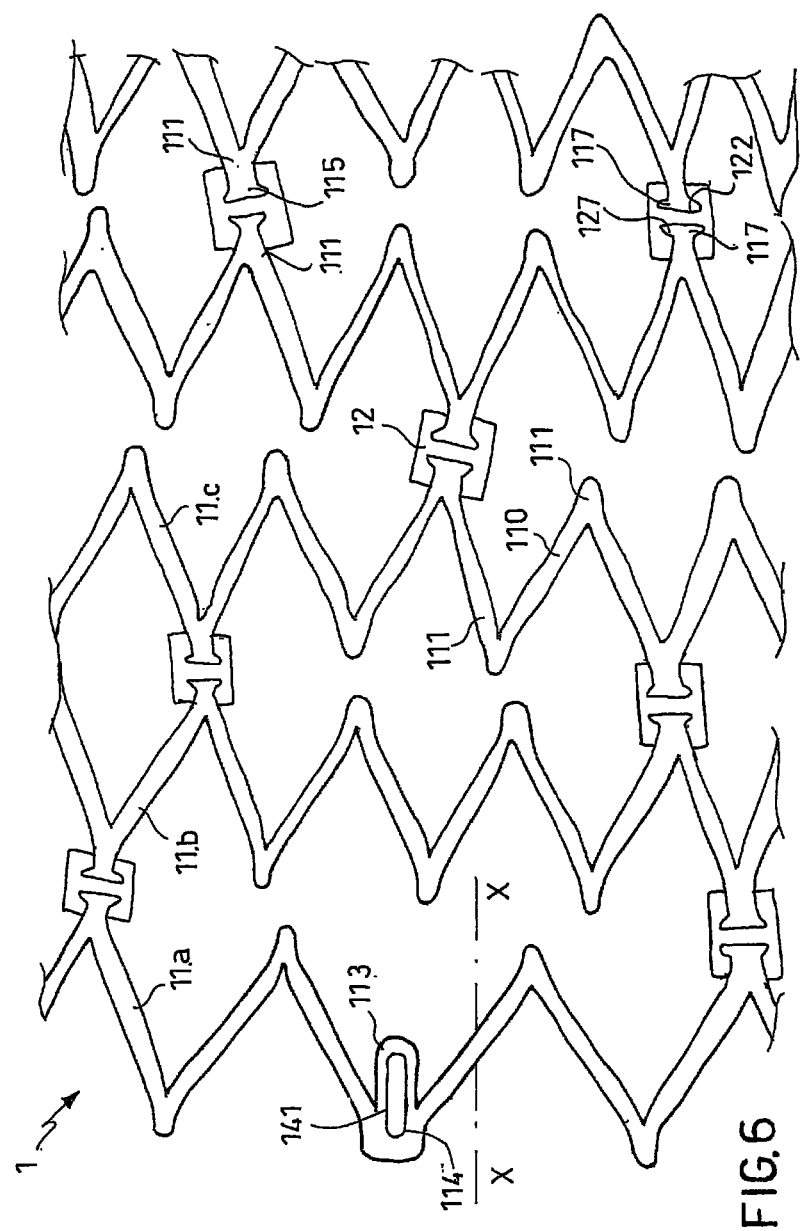

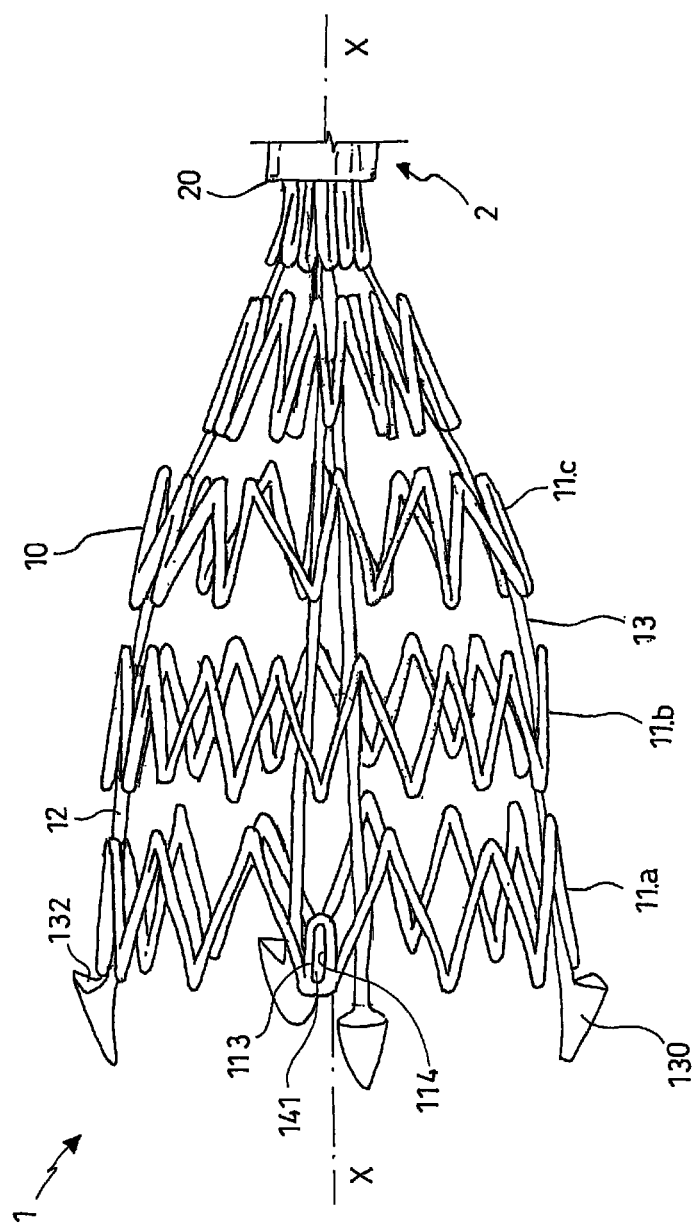

ENDOLUMENAL PROSTHESIS

BACKGROUND OF THE INVENTION

This invention relates to an endolumenal prosthesis, or stent, for use in passages or ducts in living bodies, and above all, in the human body. This endolumenal prostheses can be used to restore the passage in blood vessels, restricted or blocked by pathological phenomena such as stenosis for example. This endolumenal prosthesis can also be used in biliary ducts or other similar organs.

The present invention relates to a type of endolumenal prosthesis that is positioned in a radially contracted position inside the selected duct. Once it is in position, the prosthesis is expanded until it reaches the size suitable for the duct.

For certain types of endolumenal prosthesis referred to as "balloon-expandable", the expansion stage is generally completed by applying radial pressure from the interior. This pressure is generally applied by means of an element called a balloon that can be expanded radially by the introduction of a pressurised fluid.

These "balloon-expandable" prostheses are realised for example in stainless steel or in chromium cobalt alloys.

Other types of endolumenal prostheses referred to as "self-expandable", are realised in a manner so that they assume the expanded configuration spontaneously. The expansion stage is generally completed by releasing the prosthesis from radial constriction.

These "self-expandable" prostheses are realised, for example, in extra-elastic materials or with a shape memory, such as Nitinol.

Known endolumenal prostheses or stents are generally composed of a series of rings arranged alongside each other in an axial direction and connected to each other by bridges. The rings are radially contractible and expandable. In turn, the bridges are often elastic in the axial and circumferential directions.

Thanks to this structure, and above all, thanks to the radially contractible and expandable rings, stents are able, first of all to assume both a contracted and an expanded configuration. Moreover, thanks to the bridges being elastic in axial and circumferential directions, the stent is able to follow all the movements and deformation of the blood vessel during its operational life.

Although these endolumenal prostheses are very satisfactory from many points of view, especially in relation to their great flexibility and elasticity that permits easy insertion of the contracted prosthesis into narrow twisting passages, it can occur that said stents are not sufficiently adapted to support the continuous stress applied by the walls of the blood vessel in operational life.

In particular, the type of stress that has shown to be the most dangerous for the prosthesis is the so-called "fatigue" stress, derived from loads that can vary with time. This stress is translated as a state of strain which oscillates around an average value.

Generally fatigue stress can lead to the rupture of a mechanical component even if a stress peak that exceeds the static rupture limit of the component is never registered during the period of the operational life.

In the specific case of endolumenal prostheses or stents, the fatigue stresses become particularly dangerous for the bridges that connect the rings together.

In spite of the very strict tests to which stents are subject before use in human patients, unfortunately it can still occur that a bridge will break because of fatigue.

The rupture of a bridge gives origin to two fragments and two fracture surfaces. The two fragments that are no longer connected to each other, are far less flexible than the complete bridge and less adapted to following the deformation of the blood vessel walls on which they are supported.

Because of this situation, the two fracture surfaces do not possess the same characteristics as the other stent surfaces, especially treated during the manufacturing process for contact with the blood vessel wall. Moreover, often the fracture surfaces have pointed edges which even sometimes form a cutting edge.

Therefore it is clear that a fracture of this type can result in dangerous stress for the wall of the blood vessel. This stress is dangerous because immediately, in the worst case, it can lead to the perforation of the wall. In less serious cases, over a longer period of time, it can lead to local thickening of the wall with the obvious annulment of the effect that was aimed at with the original implant of the stent.

SUMMARY OF THE INVENTION

The aim of the present invention is to propose an endolumenal prosthesis, having the structural and functional characteristics able to overcome the aforesaid problems which are present with the known art.

In particular, the task of the present invention is to propose an endolumenal prosthesis able to resolve the problem of possible rupture caused by fatigue.

This aim and task are achieved by means of an endolumenal prosthesis of the type described in claim 1.

Further embodiments are described in the ensuing claims.

BRIEF DESCRIPTION OF THE DRAWINGS

Further characteristics and advantages of the prosthesis according to the invention will be made clear from the description provided below of certain preferred embodiments thereof, given by way of example only and not to be considered as limiting in any way, with reference to the appended figures wherein:

FIG. 6 shows a plane view of a development of an expanded endolumenal prosthesis, according to an embodiment of the invention;

FIG. 11.*c* shows the endolumenal prosthesis of the kit shown in FIG. 11.*b* in an expanded condition;

DETAILED DESCRIPTION OF THE PREFERRED EMBODIMENTS

Figure 1:
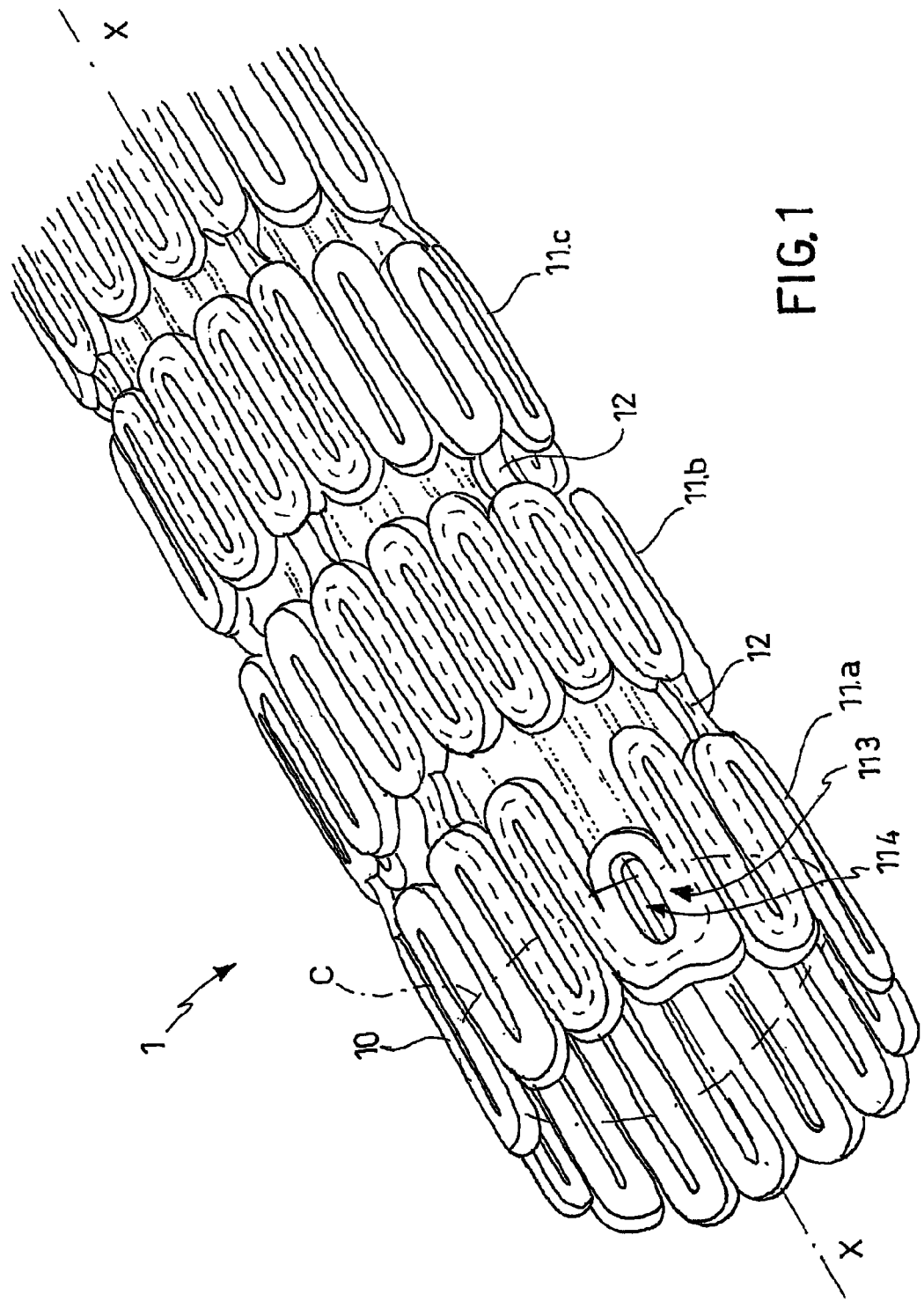
FIG. 1 shows a perspective view of a contracted endolumenal prosthesis, according to an embodiment of the invention.
Figure 2:
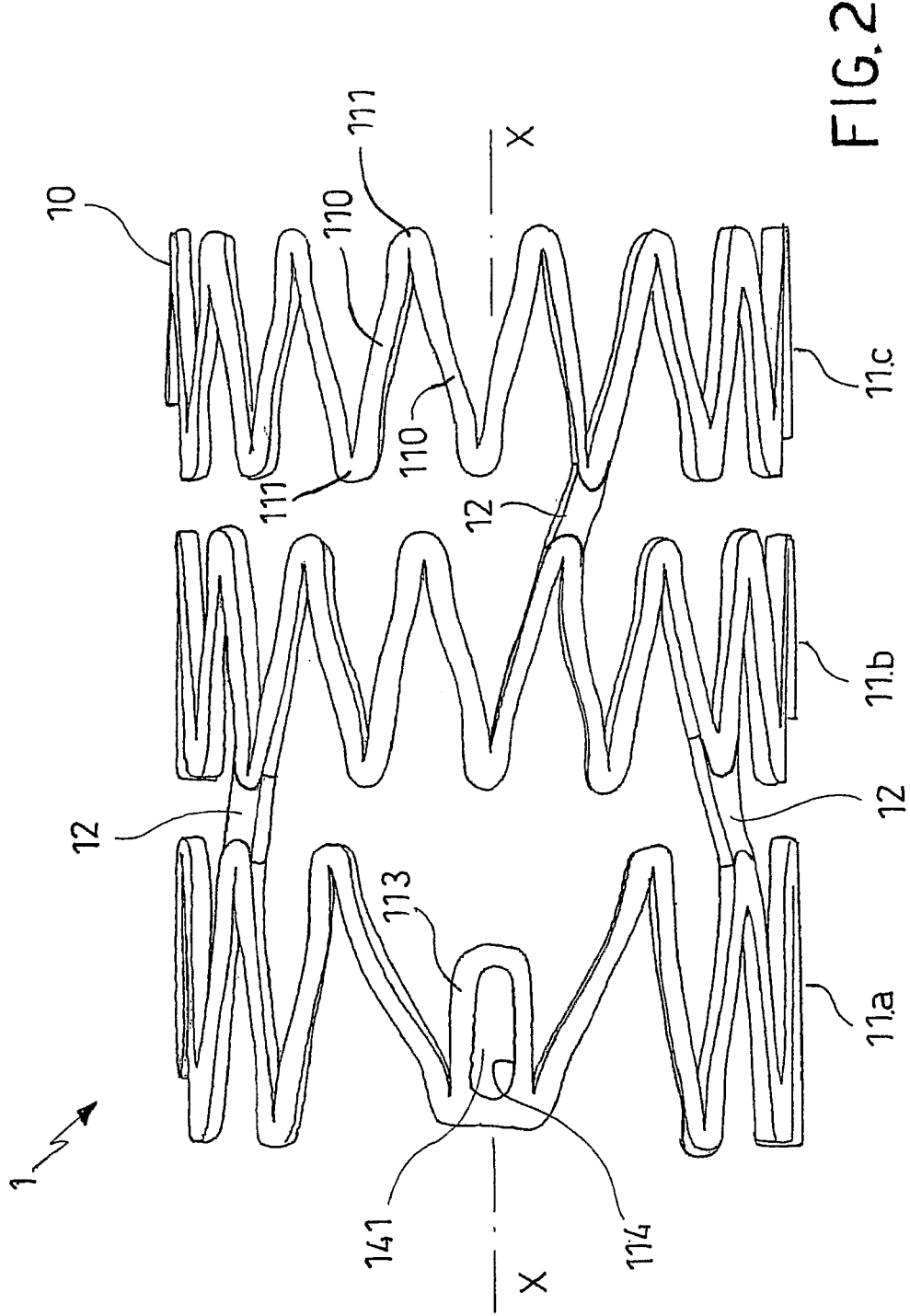
FIG. 2 shows a side elevation view of an expanded endolumenal prosthesis according to an embodiment of the invention.

In reference to the aforesaid figures, the numeral 1 refers throughout to an endolumenal prosthesis or stent. Stent 1 can be indiscriminately either the "balloon-expandable" or "self-expandable" type.

In accordance with a general form of the present invention, the endolumenal prosthesis 1, comprises a tubular body 10 adapted to convert from its contracted condition to an expanded or partially expanded condition.

The term "contracted condition" refers to the state of the stent 1 when it is radially compressed in a manner so that it presents an external diameter and a radial dimension smaller than the diameter and dimension when it is in use.

For example, the stent 1 is arranged in its contracted condition when it is received or placed onto a transport and delivery device 2 (catheter) adapted to pass through a duct or vessel as far as the zone to be treated.

Figure 9:
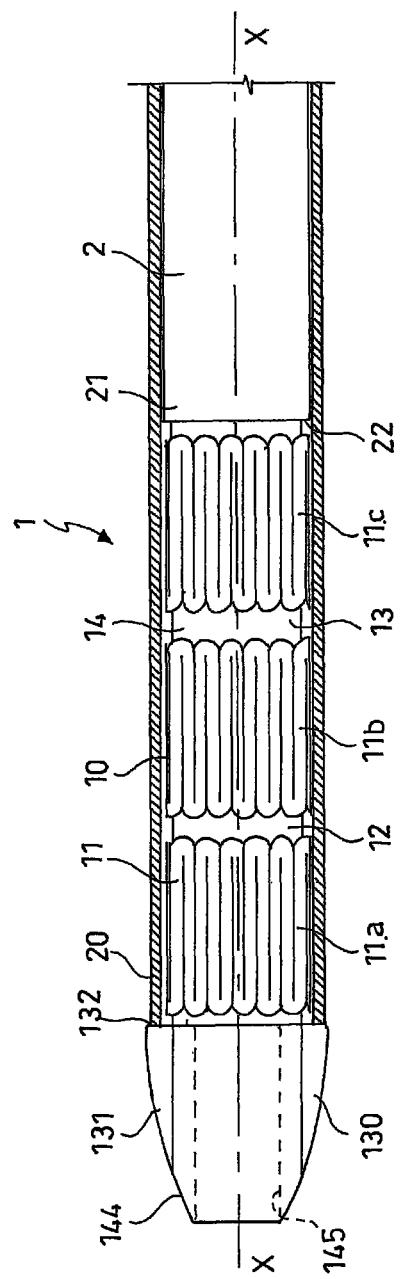
FIG. 9 shows a partial section side view of a kit according to the invention.
Figure 10A:
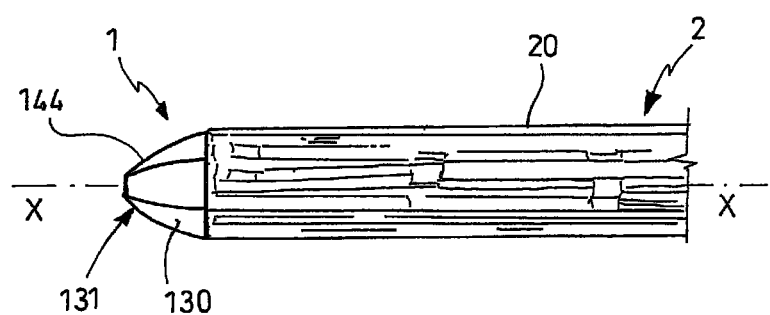
FIGS. 10.*a*, 10.*b* and 10.*c* show a kit similar to that shown in FIG. 9 wherein the endolumenal prosthesis assumes respectively three different configurations.
Figure 10B:
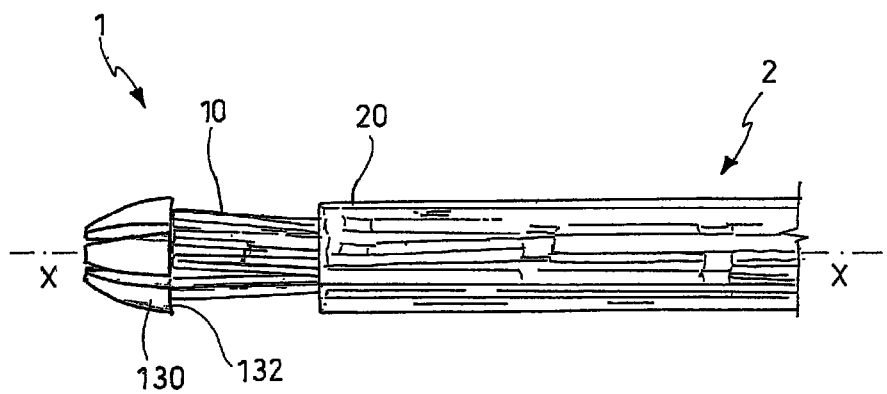

In the example shown in FIGS. 9 and 10, the self-expandable stent is placed on a catheter 2 and enclosed in a sheath 20 which, compressing it radially, maintains it in its contracted state.

Figure 11A:
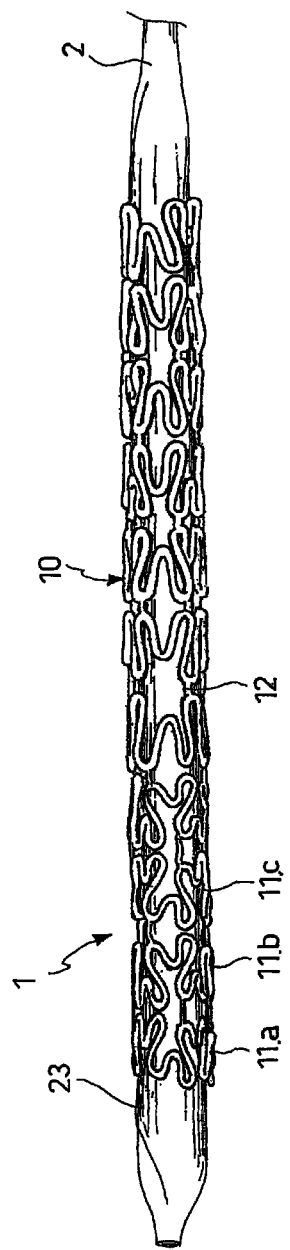
FIGS. 11.*a* and 11.*b* show a kit according to the invention wherein the endolumenal prosthesis assume respectively two different configurations.
Figure 11B:
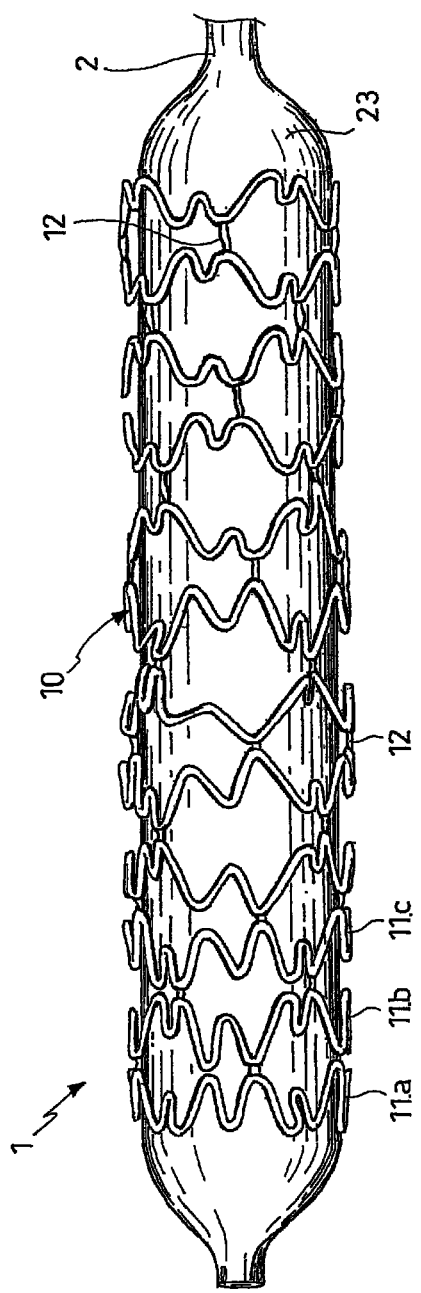
Figure 11C:
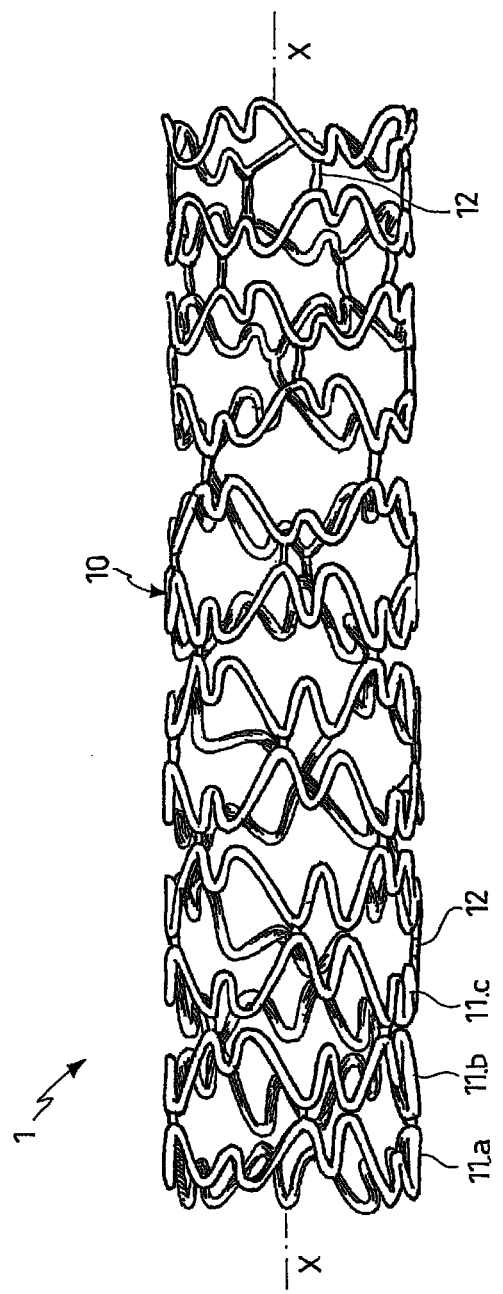

On the other hand, in the example shown in FIG. 11, the balloon-expandable stent is placed in its contracted configuration on the deflated balloon 23 of a catheter 2.

The term "expanded condition" refers to the condition wherein the stent 1 is radially widened and when in use, it is placed in contact with the internal surface of the walls of a duct or vessel.

For example, the stent 1 is placed in expanded condition when it is set in its permanent position in the zone to be treated in a duct or vessel.

For example, in the case of a self-expandable stent, once the stent 1 has been moved into position by means of the catheter, the sheath 20 that compresses it radially, is then removed, and the stent 1 converts spontaneously to its expanded condition (See FIG. 10.*c*.).

In the case of a balloon-expandable stent, on the other hand, once the stent 1 has been moved into position by the catheter 2, the balloon 23 is inflated. By pressing radially on the interior of the stent 1, the balloon 23 converts the stent 1 to its expanded condition (See FIG. 11.*b*).

The tubular body 10 is developed along a longitudinal axis X-X.

The term "longitudinal axis" refers to an axis of symmetry of a cylindrical body for example, or the axial direction of the main extension of a tubular body.

Every direction parallel to the X-X axis is therefore defined as an axial direction.

The tubular body 10 comprises a plurality of coils 11.*a*, 11.*b*, etc. Said coils define meandering courses which are preferably closed. In the stent 1 shown in the appended figures, the coils are developed in a substantially circumferential direction (shown by the letter C in FIG. 1).

The term "coil" refers to an element that is developed according to a zig-zag course or a backward-forward course around a main extension direction. In the case of the coils that form stent 1 shown in the appended figures, the main direction is the circumferential direction C, around which the zig-zag course progress is developed.

Each of the said coils 11 comprise portions with an arm or arms 110, and portions with a loop or loops 111, that connect two following arms 110 to form the meandering course.

According to one embodiment, the arms 110 have a substantially straight-line form, and the loops 111 substantially form a circular crown shape sector.

According to another embodiment the arms 110 are shaped in a curved line such as an "S" shape for example.

At least one bridge 12 connects two coils, for example two adjacent coils such as 11.*a* and 11.*b*, or two non-adjacent coils such as 11.*a* and 11.*c*.

According to another embodiment of stent 1 represented in FIG. 1, the bridge 12 is developed in a substantially straight line direction with an extension orientated in an approximately axial direction substantially parallel to axis X-X.

According to other embodiments of stent 1, bridge 12 is developed even further and can also have its own circumferential extension.

Figure 7:
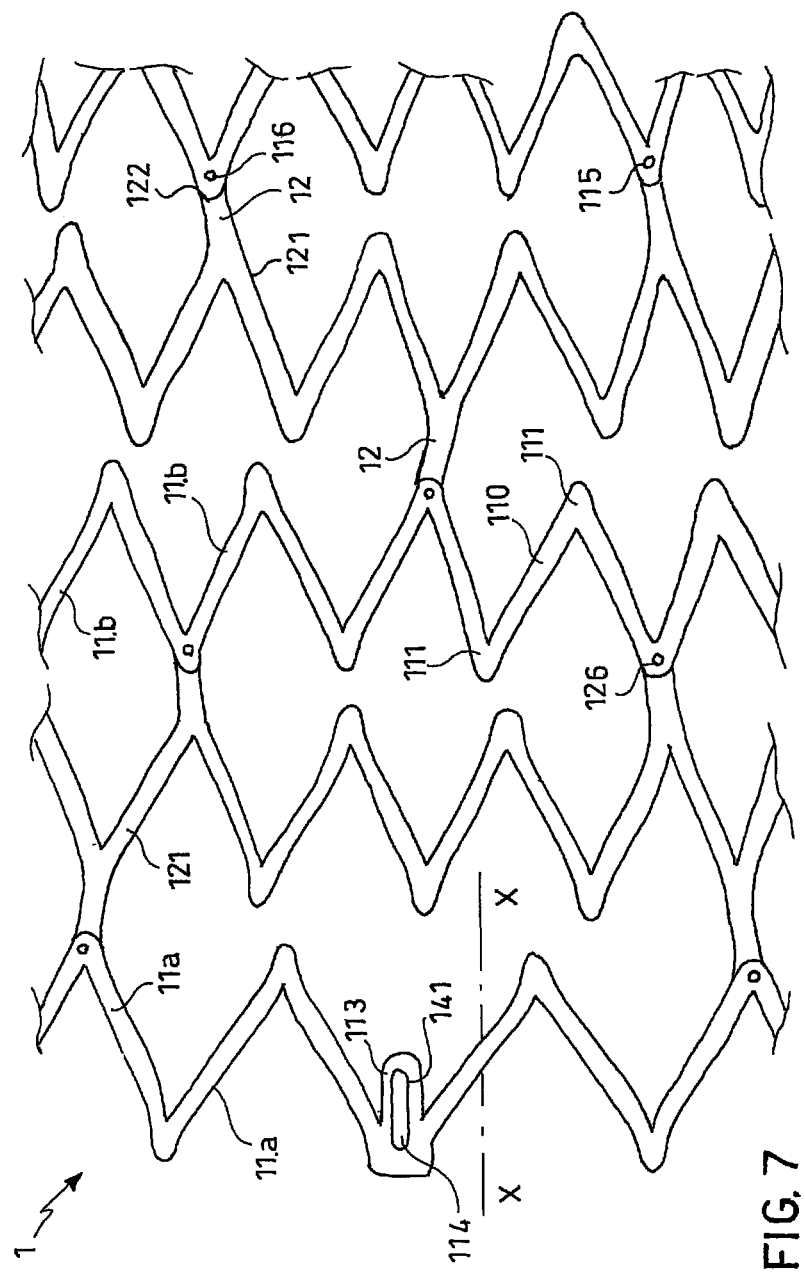
FIG. 7 shows a plane view of a development of an expanded endolumenal prosthesis, according to an embodiment of the invention.

According to another embodiment of stent 1 according to the invention (for example the embodiment shown in FIG. 7), the bridge 12 is developed in a circumferential direction until it forms a pseudo-coil 121 or at least a part thereof.

The term pseudo-coil 121 refers to a structure that is very similar to one of the coils 11 described above. The only difference between the pseudo-coil 121 and the coil 11, is the material with which the two structures are realised, and therefore the preservation of the structures in relation to time. The pseudo-coil 121 is part of the bridge 12 and is therefore realised in the same material as bridge 12.

The materials used for the different structures, coils 11, bridges 12 and pseudo-coils 121, will be described further on.

Advantageously, a plurality of bridges 12 is positioned between adjacent coils, such as 11.*a* and 11.*b* for example.

Figure 14:
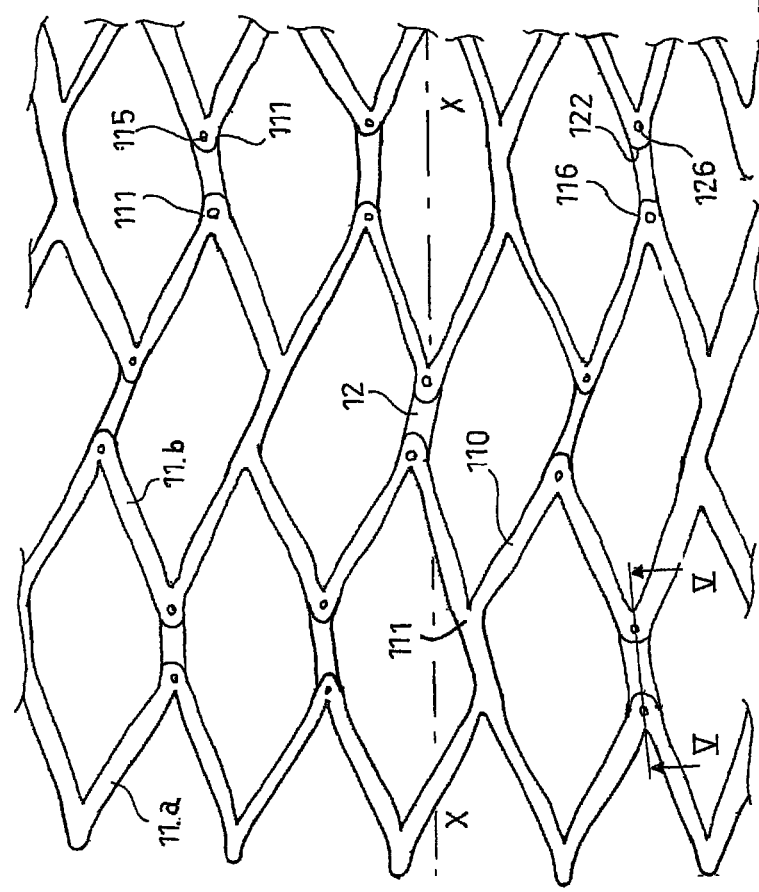
FIG. 14 shows a plane view of a development of an expanded endolumenal prosthesis according to an embodiment of the invention.

According to the embodiment shown in FIG. 14, each single loop 111 of each single coil, for example 11.*b*, is connected by a bridge 12 to the respective loop 111 of the adjacent coil, for example 11.*a* or 11.*c*.

Figure 3:
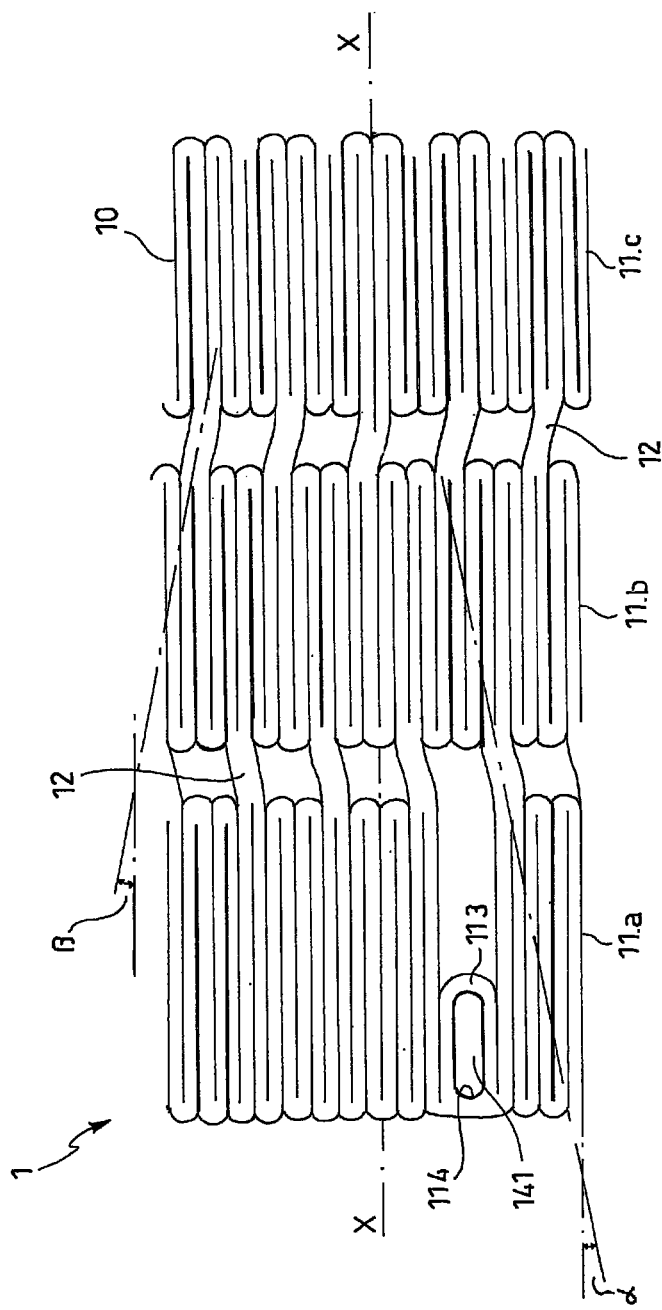
FIG. 3 shows a plane view of a development of a contracted endolumenal prosthesis according to an embodiment of the invention.

According to the embodiment shown in FIG. 3, the at least one bridge 12 has a slightly sloping direction in relation to the axial direction of the tubular body 10. The direction of the bridge 12 is, for example, sloped at an angle which is identified by the reference symbols α or β.

Preferably, all the bridges 12 between at least two adjacent coils 11 are parallel with each other.

According to one embodiment, by following the stent 1 in a longitudinal direction, for example, starting from one proximal extremity and moving towards a second distal extremity of the stent, it can be seen that the bridges 12 alternate with each other with directions having an opposite slope (respectively α and β) in relation to an axial direction. Advantageously α and β are the same size, but slope in the direction opposite to the axial direction.

According to the embodiment of stent 1 according to the invention shown in the figures from 4 to 8, at least some of the loops 111 from which a bridge 12 branches off, comprise fixation actuators 115. Fixation actuators 115 are geometrical alterations of the loop realised in a manner that makes the attachment of bridge 12 to loop 111 stronger and more secure.

Figure 4:
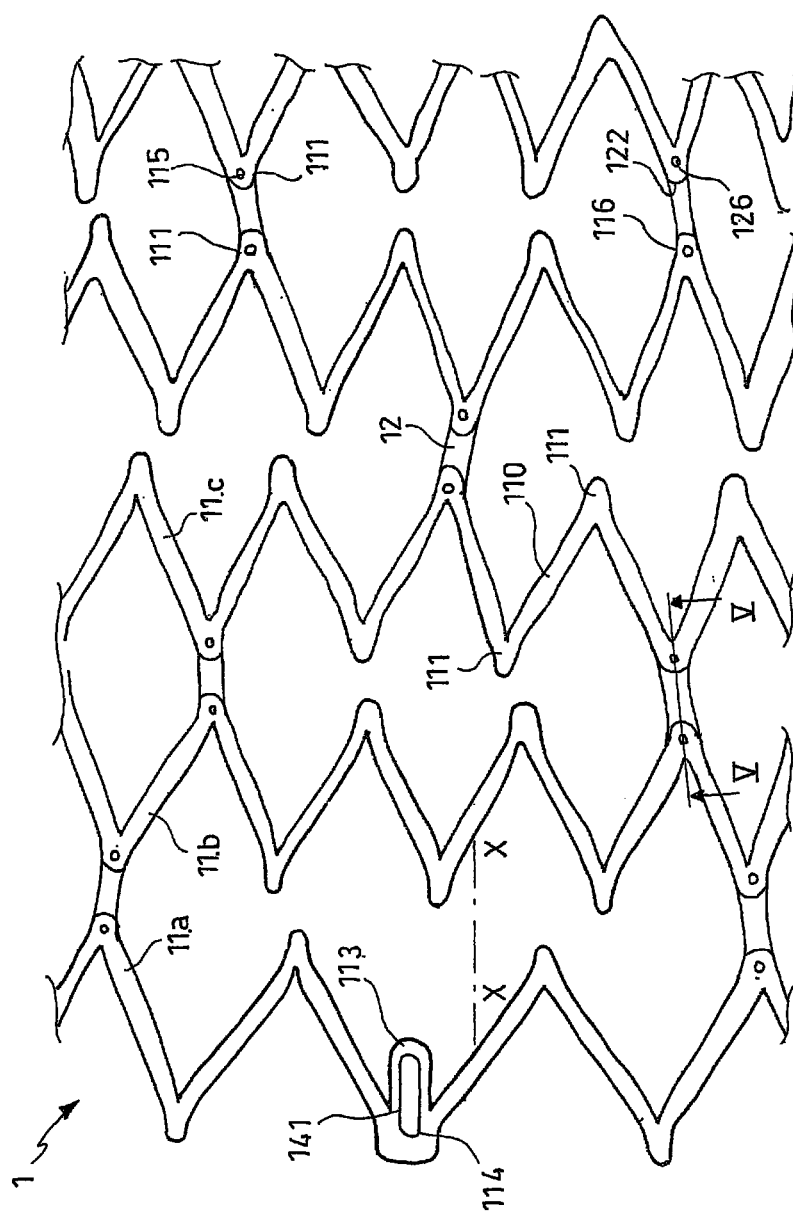
FIG. 4 shows a plane view of a development of an expanded endolumenal prosthesis, according to an embodiment of the invention.
Figure 5A:
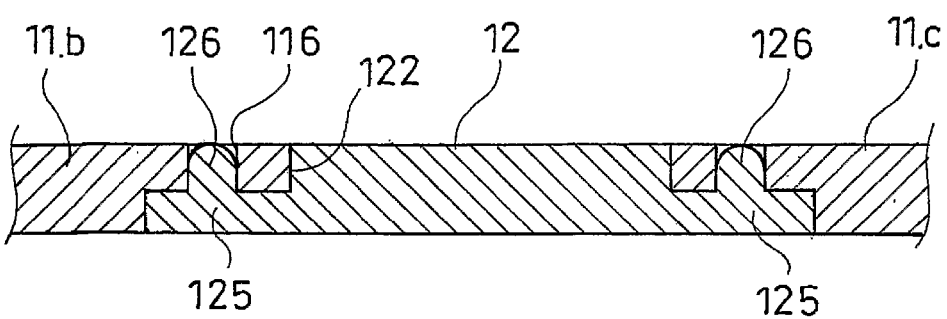
FIGS. 5.*a* and 5.*b* show two possible section views along the plane V-V of FIG. 4.
Figure 5B:
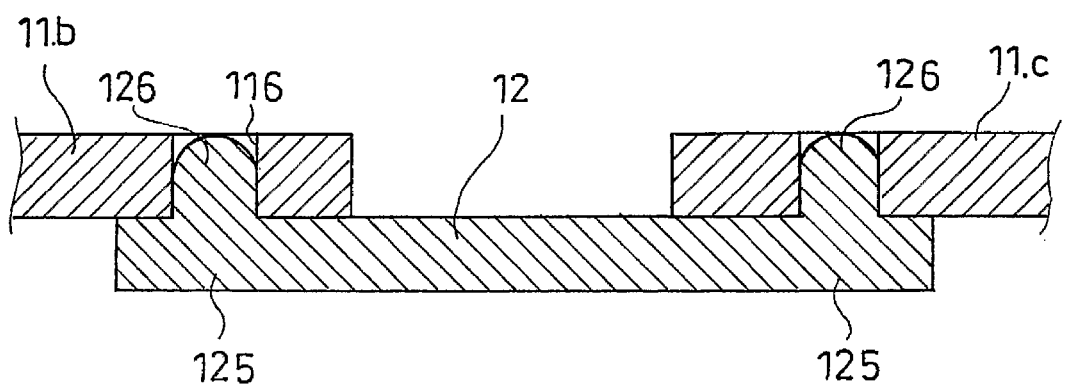
Figure 8:
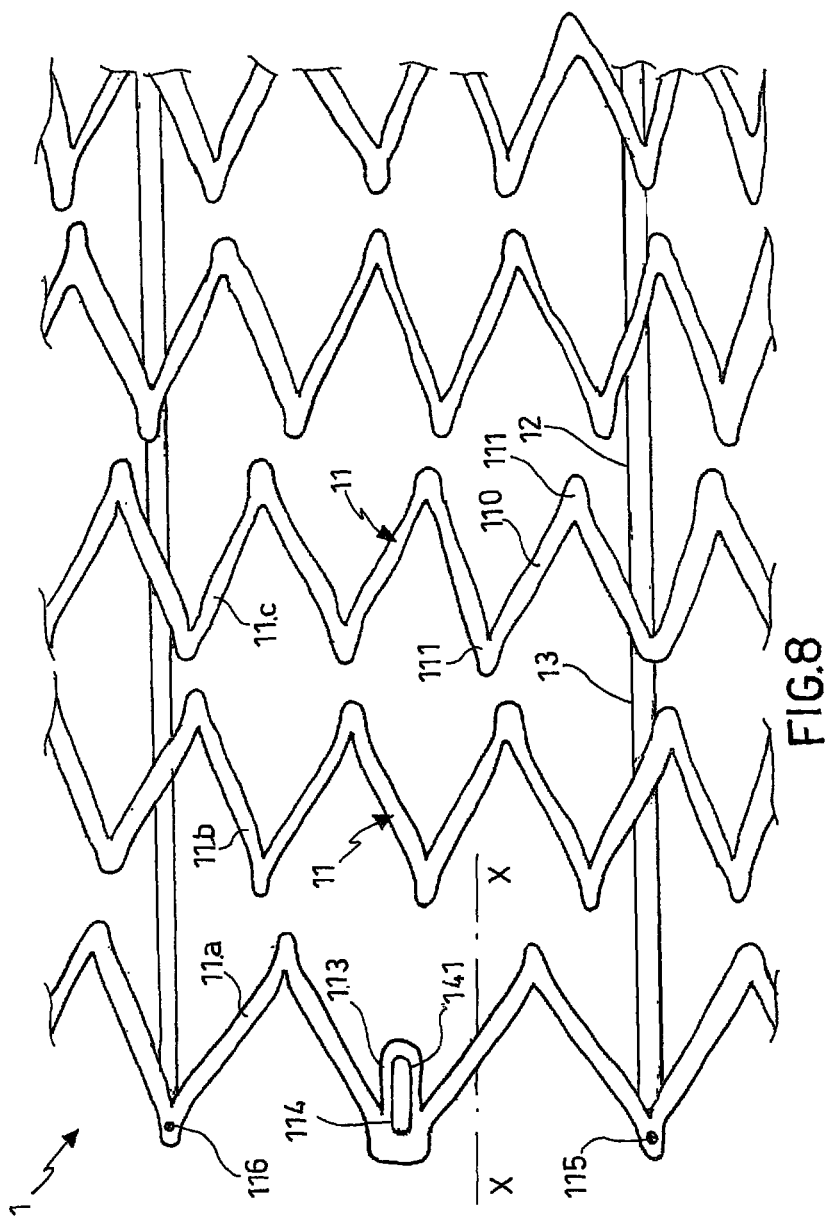
FIG. 8 shows a plane view of a development of an expanded endolumenal prosthesis, according to an embodiment of the invention.

According to the embodiment shown in FIGS. 4, 5 and 8, the fixation actuators 115 comprise a hole 116 practiced in the width of the coil 11 at the height of the loop 111.

According to the embodiment in FIG. 5.a, the geometry of the bridge 12 comprises a profile 122 that replicates with great accuracy the profile contour of the loop 111.

According to the embodiment of FIGS. 4 and 5, the bridge 12 also comprises a tab 125 from which branches off a peg 126. The tab 125 and the peg 126 are formed integrally from the bridge 12 itself and therefore they are an integral part of the bridge. The peg 126 is engaged inside the hole 116, to guarantee the fixation of the bridge 12 to the loop 111.

Once again, according to the embodiment shown in FIG. 6, the fixation actuators 115 comprise specially shaped protrusions 117 positioned on the exterior of the width of the coil 11 at the height of loop 111.

In this case, the geometry of the bridge 12 comprises a profile 122 that replicates with great accuracy the profile of loop 111. In turn, the profile 122 comprises portions of undercut 127 complementary with the shaped protrusions 117 of loop 111. The undercut portions 127 wrap around the shaped protrusions 117 to guarantee the fixation of bridge 12 to loop 111.

The fixation actuators 115 are thus destined to provide shape coupling between the loop 111 and the respective bridge 12.

The shape coupling can be obtained on macroscopic scale, as in the examples described above, or on a more reduced scale. Shape coupling can be obtained for example, by means of an incised line on the surface of the loop 111 or by means of high-level loop porosity.

In these cases, the geometry of the bridge 12 comprises a complementary incised line to that made on the surface of loop 111, or respectively, a series of micro-protrusions complementary to the surface porosity of the loop surface 111.

Shape coupling will therefore guarantee that bridge fixation onto the coil is more efficient and reliable.

Advantageously when the said stent is self-expandable, each coil 11 will be made of superelastic material. According to a different embodiment, each coil 11 is made of hardened pseudo-elastic material.

In other words it is possible to use a material that is in an austenitic state at room temperature (that is—with a temperature higher than the end of transformation in austenite Af less than 15° C.) when it is rebaked, to which is then applied a sufficient hardening treatment, for example, higher than 30%, that permits an elastic recovery to deformation of 3%-4% or higher. Preferably a hardening treatment equal to 50% should be applied. For the sake of simplicity, hereafter the material identified above will be referred to with the term "Superelastic material".

According to one embodiment, said coils 11 are in a so-called shape memory material.

Advantageously, said coils 11 are in Nitinol, or a Nickel and Titanium based alloy, for example with a nominal weight percentage of 55.8% of Nickel.

For example, it is possible to use a material having a austenite-martensite transition phase wherein, if in re-baked or stress relieved state, during heating, the highest temperature of the end of transformation into austenite Af is lower than 15° C. For the sake of simplicity the alloy identified above will be referred to as "Nitinol".

Advantageously, when said stent is balloon-expandable, each coil 11 is made of stainless steel.

For example it is possible to use stainless steel of the type classified as AISI 316 L according to the American Iron and Steel Institute standards. This stainless steel alloy has the following weighted standard chemical composition: Carbon 0.035%, Phosphorous 0.04%, Sulfur 0.03%, Manganese 2%, Silicon 0.75%, Chromium 16-18%, Nickel 10-15%, Molybdenum 2-3% and iron to create balance. For simplicity, the alloy identified above will be referred to as "stainless steel".

Advantageously when said stent is of the balloon-expandable type, each coil 1 is made of a non-magnetic alloy of Nickel-Cobalt-Chromium-Molybdenum for surgical implants.

For example it is possible to use an alloy of the type classified as UNS R30035 according to the Unified Numbering System for Metals and Alloys. This alloy has the following standard composition: Carbon 0.025% maximum, phosphorus 0.015% maximum, Sulfur 0.01% maximum, Manganese 0.15% maximum, Silicon 0.15% maximum, Chromium 19-21%, Nickel 33-37%, Molybdenum 9-11%, Titanium 1% maximum, Boron 0.01% maximum, iron 1% maximum and Cobalt to create balance.

An alloy of this type is marketed under the name "Carpenter MP35N" which is a trademark owned by SPS Technologies, Inc. For the sake of simplicity, hereafter the alloy identified above will be referred to as "Chromium-Cobalt alloy".

According to one embodiment, each coil 11 of said stent 1 is obtained by the cutting of a tubular element, preferably using laser cutting.

According to a possible embodiment, each coil 11 is made in a single piece from a tubular element by means of cutting action, for example laser cutting.

The materials described up to this point with which the coils 11 according to the invention are realised, are persistent materials. In other words the coils 11 according to the invention realised in superelastic material, in Nitinol, in stainless steel, or in Chromium-Cobalt alloy, remain practically unaltered in size and geometry during their operational life inside a vessel or duct where they are implanted.

In comparison to the persistent materials with which the coils 11 of stent I according to the invention are realised, the bridges 12 instead are realised in a material that is commonly defined as biodegradable or bioerodibile or, preferably, bioabsorbable. in other words, the material used to realise each bridge 12 has the property of dissolving in the natural context of the vessel or duct in which the stent has been implanted (for example in the blood in blood vessels). The phenomenon that makes the bioabsorbable material dissolve can be of a chemical, electrochemical or physical nature, according to the type of material used.

According to one embodiment the bridge 12 is realised with a bioabsorbable polymer. Bioabsorbable polymers that are particularly suitable for employment in the present invention are: PDLA or poly-(D-lactic acid), PLLA or poly-(L-lactic acid), PGA or poly-(glycolic acid).

Further bioabsorbable polymers suitable for use are the following: poly-caprolactone, poly-(lactide-co-glycolide), poly-(ethylene-vinyl acetate), poly-(hydroxybutyrate-co-valerate), poly-dioxanone, poly-orthoester, poly-anhydride, poly-(glycolic acid-co-trimethylene carbonate), poly-phosphoester, poly-phosphoester urethane, poly(amino acids), cyanoacrylates, poly-(trimethylene carbonate), poly-(iminocarbonate), copoly-(ether-esters) (e.g. PEO/PLA), poly-alkylene oxalates, poly-phosphazenes and biomolecules such as fibrin, fibrinogen, cellulose, starch, collagen, hyaluronic acid, poly-N-alkylacrylamides, poly-depsi-peptide carbonate, and poly-ethylene-oxide based polyesters.

The bridges 12 in bioabsorbable polymer can be realised using any type of standard technologies used for producing this type of polymer. For example the bridges 12 in polymer can be advantageously realised using fusion, hot-molding, extrusion, sintering, or any other type of technological process that satisfies the specific requirements.

The connection between the bridge 12 in polymer and the coil 11 can be obtained independently from the presence of the fixation actuators 115, for example by means of gluing. The polymer used as the adhesive can be the same in which the bridge is realised, or some other bioabsorbable polymer, according to specific requirements.

According to certain embodiments, the bridges 12 are realised using bioabsorbable metallic materials.

According to a possible embodiment the bridge 12 is realised using a Magnesium alloy.

For example it is possible to use an alloy of the type classified as UNS M18430 according to the Unified Numbering System for Metals and Alloys. This alloy has the following standard composition: Yttrium 3.7-4.3%, Rare earths 2.4-4.4% (Rare earths consist of Neodymium 2.0-2.5%, and the rest being made up of heavy rare earths, mainly Ytterbium, Erbium, Dysprosium and Gadolinium), Zirconium 0.4% minimum, and Magnesium to create a balance.

An alloy of this type is marketed under the name "Elektron WE43", owned by Magnesium Elektron of Manchester, UK. For the sake of simplicity hereafter the alloy described above will be referred to as "magnesium alloy".

The bridges 12 in magnesium alloy can be realised by means of any type of standard technological process for this type of alloy. For example the bridges 12 in magnesium alloy can be advantageously realised using fusion, hot or cold molding, sintering, laser processing, or any other kind of technological process that satisfies the specific requirements.

The connection between the bridge 12 in magnesium alloy and the coil 11 can be obtained independently of the presence of the fixation actuators 115, for example by welding, or gluing, according to the specific requirements. Welding can be performed using a technology in protective atmosphere (for example with TIG, Tungsten Inert Gas). The polymer used as an adhesive can be a bioabsorbable polymer among those listed above.

According to a possible embodiment the bridge 12 is realised with a binary mixture of calcium oxide (CaO) and phosphorous pentoxide (or phosphoric anhydride) ($P_2O_5$).

For example it is possible to use a binary mixture composed of 5-50% of calcium oxide (CaO) and 50-95% of Phosphorous pentoxide ($P_2O_5$). Preferably the binary mixture is composed of 15-25% Calcium oxide (CaO) and 65-85% Phosphorous pentoxide ($P_2O_5$). This binary mixture can also contain small quantities of Calcium fluoride ($CaF_2$), water ($H_2O$) and other oxides of Magnesium, Zinc, Strontium, Sodium, Potassium, Lithium or Aluminium.

For the sake of simplicity, hereafter the mixture described above will be referred to by the term "Calcium-Phosphorous mixture".

The bridges 12 in Calcium-Phosphorous mixture can be realised using any one of the standard technologies used for processing this type of material. For example the bridges 12 in Calcium-Phosphorous mixture can be advantageously realised using fusion, hot molding, or any other technological process that satisfies the specific requirements.

The connection between the bridge 12 in Calcium-Phosphorous mixture and the coil 11 can be obtained independently of the presence of the fixation actuators 115, for example by welding or gluing, according to specific requirements. The polymer used as an adhesive can be any one of the bioabsorbable polymers listed above.

According to certain possible embodiments, for example that shown in FIG. 14, certain bridges are realised in persistent materials and are alternated along the circumferential direction with other bridges realised in bioabsorbable material.

Figure 12A:
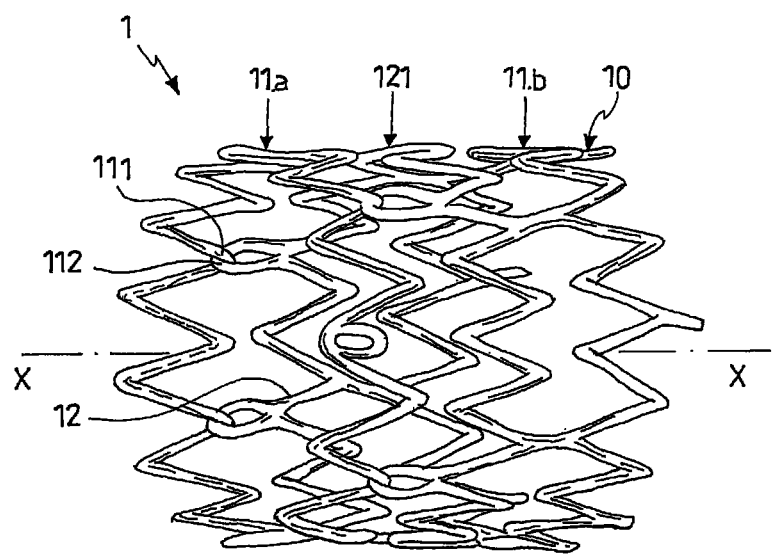
FIGS. 12.*a* and 12.*b* show a perspective view of two further embodiments of the endolumenal prosthesis according to the invention.
Figure 12B:
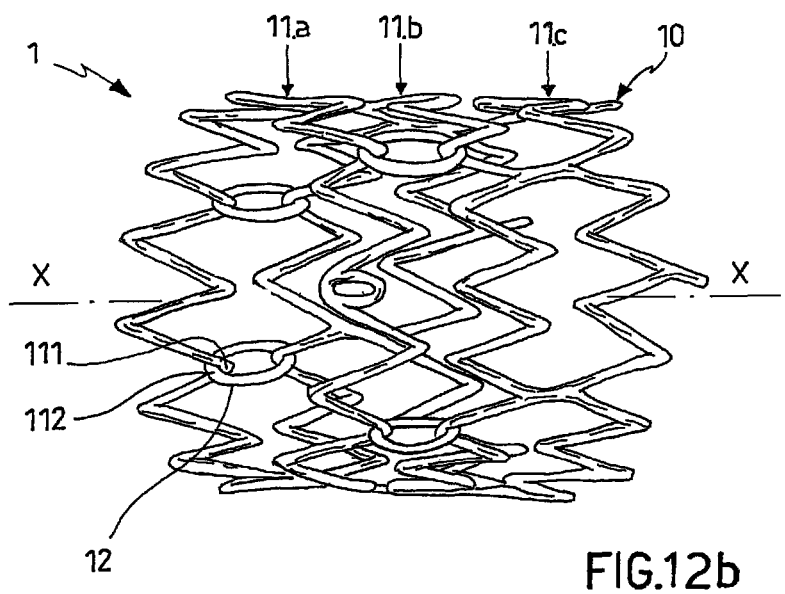
Figure 13:
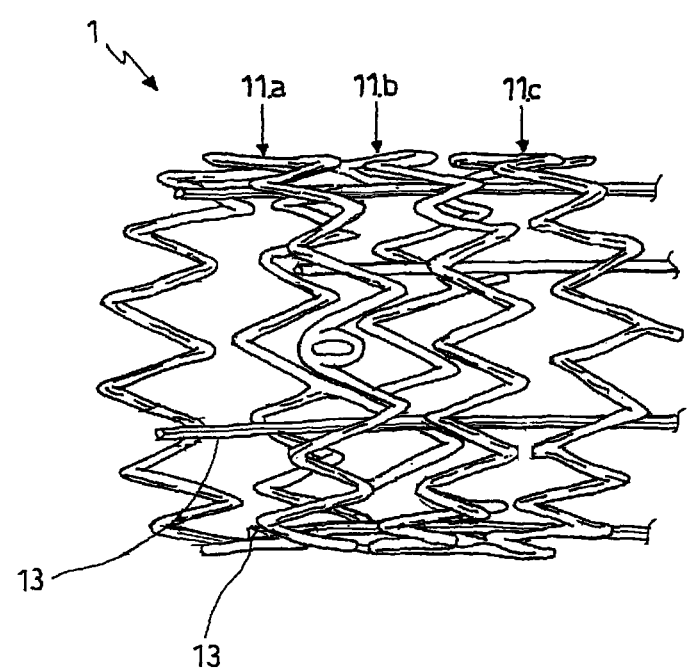
FIG. 13 shows a perspective view of an embodiment of the endolumenal prosthesis according to the invention similar to that shown in FIG. 8.

According to the embodiments shown in FIGS. 12.a and 12.b, at least certain connections between the bridges 12 in bioabsorbable material and the coils 11 in persistent material, are realised in chain form. In other words the bridge 12 forms a loop 112, adapted to enfold the loop 111 of coil 11.

This type of chain connection permits the guarantee of considerable resistance to traction strain along the X-X axis even when the superficial adhesion between the bioabsorbable material of the bridge 12 and the persistent material of coil 11 does not reach top performance levels.

According to the embodiment shown in FIGS. 8, 9 and 10, the bridge 12 assumes the form of a beam 13. The beam 13 is a structure that has a predominantly axial development and which unites more than two coils 11. As is clearly shown in FIGS. 8 and 10.c, the beam 13 is positioned inside the coils 11 and is connected to their radially internal surface. If required, this surface can also comprise fixation actuators 115 similar to those described above and destined to provide shape coupling for at least some of the coils 11 and the beam 13.

The shape coupling therefore guarantees that the fixation of the beam on the coil is much more efficient and reliable.

According to one embodiment, a plurality of beams 13 is present, for example four as shown in the FIG. 10. When the stent 1 is in contracted position (See FIG. 9) the beams approach one another until they are in reciprocal contact.

According to one embodiment of the stent 1 according to the invention, the contact obtained between the beams 13 permits the realisation of a tubular structure 14 inside the coils 11 when the stent 1 is in its contracted configuration.

The tubular structure 14 allows the use of a particular transport and delivery device which, unlike known devices, does not support the stent 1 from the interior.

The transport and delivery device for the stent 1 comprising the tubular structure 14, comprises a catheter 2 and a sheath 20 distally longer than the catheter 2. By means of its distal extremity, the catheter 2 furnishes an axial support for stent 1. On the other hand, the sheath 20 furnishes the radial containing system for the stent 1.

The distal extremity 21 of the catheter 2 therefore comprises a shoulder 22 that is supported on the surface of the proximal extremity of the tubular structure 14.

The sheath 20 has a length that distally exceeds that of the catheter 2 for a distance equal to the length of the stent 1.

The tubular structure 14 is adapted to receive therein, a guidewire for the correct positioning of the stent 1 inside the vessel, using a method per se known. For this reason the distal extremity 144 of the tubular structure 14 defines an opening 145 adapted to receive a guidewire.

According to a possible embodiment of the stent 1 according to the invention, each of the beams 13 comprises at its distal extremity, a keel 130. In this manner, when the stent 1 is in its contracted condition and the beams are in contact with one another, the plurality of keels 130 creates a tip 131.

Each of the keels 130 define a shoulder 132 that has a greater radial extension than that of the coils 11 and that is therefore adapted to define a support in axial direction for the sheath 20.

The presence of the keels 130 and the tip 131 at the distal extremity of the stent 1 when it is in contracted condition, will therefore facilitate the insertion operation of the stent 1 inside ducts or vessels of the patient.

According to one embodiment, on end coil (for example the coil 11.a positioned at the distal end 11.a) comprises a marker 141 realised in radiopaque material.

In fact in the case where the coils 11 of the stent 1 are realised, for example, in extra-elastic material or in Nitinol, and the bridges 12 are realised, for example, in magnesium alloy, the stent would result as absolutely invisible under radioscopy.

A stent that is not visible to radioscopy poses very serious problems for the operator who implants it in a patient conventionally using radioscopy equipment to follow the movement and positioning of the stent along the patient's vessels.

According to one embodiment, the coil 11 comprises at least one frame 113 defining a slot 114 and inside the slot 114 is foreseen the radiopaque marker 141. Advantageously, the frame 113 is made integrally in the tubular body 10 obtained by laser cutting in a cylindrical wall.

Advantageously the marker 141 realised in radiopaque material is melted inside the slot 114. The radiopaque material can be any material that has greater visibility under X-ray than persistent and bioabsorbable materials used for the stent 1.

The radiopaque material used to realise the marker 141 can be chosen from Tantalum, gold, Platinum, Tungsten or other materials suitable for this purpose.

According to a possible embodiment, both the coils positioned at the distal and proximal ends of stent 1, in other words, the first and last coil, comprise respectively at least one frame 113 defining a slot 114 and the respective marker 141.

From the aforesaid description, it is easy to appreciate how the stent 1 according to the present invention, is able to satisfy the X-ray visibility requirements of the stent 1.

In fact, the presence in the stent 1 of portions such as, for example, the coils 11 realised in persistent material permits the use of the markers 141 on the stent 1 itself.

For those skilled in the art, it is immediately obvious that it would not be possible to use a marker on a stent completely realised in bioabsorbable material. In a theoretical solution of that kind, the marker would soon be free of any attachment and would be free to move along the blood vessels placing the patient in serious danger.

Thanks to the proposed stent, it is possible to perform endolumenal interventions in tortuous ducts or vessels, and to guarantee at the same time, excellent and uniform support of the treated vessel in expanded prostheses.

According to one embodiment of the stent 1 according to the invention, the parts realised in bioabsorbable material are adapted to release a drug in a controlled manner for a prolonged period of time.

The bioabsorbable parts of the stent 1, in particular the bridges 12, the beams 13 or the pseudo-coils 121, can be previously treated so that they result as porous, whether they are realised in polymer or in magnesium alloy. A pharmacologically active substance suitable for the treatment of the zone where the stent 1 is implanted, can be inserted in the porosity of the bioabsorbable material.

With this particular embodiment of the invention a controlled and prolonged drug release, in a known manner per se, can be achieved. This provides an important pharmacological contribution right in the acute stage of the treatment that has been completed with the stent 1 implant.

In a manner similar to the action of a possible drug inserted in the porous surface of the bioabsorbable material, it must be noted that the magnesium with which the bio absorbable parts of the stent can be obtained, also has positive effects on containing the cellular proliferation in the zone where the stent 1 is implanted.

Below is a list of certain of the more important mechanical characteristics of the metallic, persistent and bioabsorbable materials described above.

|   |   | Stainless steel (AISI316L) | Cr—Co (MP35N) | NiTinol | Magnesium alloy |
|---|---|---|---|---|---|
| E | Elastic module, GPa | 193 | 233 | 90 | 44 |
| $\sigma_{0.2}$ | Yield stress, MPa | 340 | 414 | — | 178 |
| $\sigma_r$ | Rupture stress, MPa | 670 | 930 | 1400 | 250 |

Together with the characteristics belonging to the materials described above, it is also important to identify certain characteristics of the stents themselves and depending, as such, both on the material employed and the geometry of design.

One extremely important characteristics of the stent is the radial force. This describes the capacity of the stent to resist circumferential loads. This can be defined as the radial force that the stent is able to exert inside a vessel once it has been correctly implanted.

Such characteristic is extremely important because it determines the capacity of the stent to maintain the treated vessel in open position. The radial force depends on the geometry, and above all on the elastic module E of the material employed. The greater the value of the elastic module, the greater the radial force that can be obtained from the stent.

A further important characteristic in the evaluation of a balloon-expandable stent is the so-called 'recoil'. In percentage, the recoil is the elastic return of the stent after expansion. In fact, during expansion, the stent is over-expanded in order to compensate for the inevitable elastic return.

The recoil of a stent can be defined as follows:

$$\text{recoil} = \frac{(\text{over-expanded diameter} - \text{expanded diameter}) * 100}{\text{over-expanded diameter}}$$

The lesser the recoil, the lesser the over-expansion necessary for efficiently implanting the stent, and consequently the lesser the risk of possible vessel dissection.

Low recoil, as well as appropriate stent geometry can be obtained thanks to a high elastic module E and a yield stress $\sigma_{0.2}$ not too high.

In the light of these considerations and the characteristics of the materials shown in the table, it is immediately possible to understand how a stent realised entirely in Magnesium alloy, for example, cannot guarantee considerable radial force because the elastic module of Magnesium alloy is relatively modest.

Since the present invention permits the use of different materials within the same endolumenal prosthesis, the project designer is able to balance the characteristics of a material with those of another.

For example, it is possible to achieve stents realised with a large amount of magnesium, but which have an acceptable radial force thanks to the stainless steel inserts.

In the light of all that has been described above, those skilled in the art will understand how an endolumenal prosthesis according to the invention resolves the problems exposed previously with reference to known art.

In particular it will now be clear how each of the embodiments of the stent 1 described above resolves the problem of possible ruptures caused by fatigue.

In fact, after an initial period immediately after the implant of the stent in position, the bioabsorbable parts dissolve, for example, in the blood, and only the coils remain, whether these are made of stainless steel or shape memory materials, perfectly positioned but unattached to each other.

As stated previously, research on stents has identified that the connecting bridges between coils are the points most subject to rupture caused by fatigue. By eliminating the bridges from the operational life of the stent, this also eliminates the problems connected with their rupture caused by fatigue.

At the same time, the temporary presence of the bridges in the initial steps of the stent implant, and during the steps immediately afterwards, guarantees excellent positioning capacity of the stent on the whole and also guarantees that the single coils assume a correct position in relation to one another.

The embodiment shown in FIG. 14 permits the operator to adjust the position of the stent along the vessel where it will be implanted, during the intervention. This operation is made possible because of the particular conformation that foresees the presence of a bridge 12 for each loop 111. In fact, such conformation permits the perfect creation of junctions between the coils that were previously uncovered during the withdrawal of the sheath 20 and those coils that are still covered by the sheath 20. This characteristic permits the operator to push the sheath 20 forward along the catheter 2 and along the stent 1 in a manner to close up the coils that had been previously open.

The operation of closing and repositioning the stent 1, results as being especially useful. The stent insertion and implant steps are extremely delicate. The slightest error when positioning the stent can provoke extremely serious consequences, to the point of needing to perform emergency surgery on the patient in order to remove an open stent in an incorrect position.

The operation of pushing the sheath 20 along the catheter 2 and along the stent 1 is not possible with traditional stents. In fact as can be seen clearly in FIG. 10.c, the loops 111 of the coils that have just been uncovered by the withdrawal of the sheath, tend to exit from the ideal profile of the stent, thus forming steps that prevent the opposite movement of the sheath 20 along stent 1.

The presence of a bridge 12 for each of the loops 111 is made possible by the fact that at least certain bridges 12 are realised in bioabsorbable material. In a traditional type stent, completely realised in persistent material, such configuration would not be possible because of the excessive amount of metal that would be present on the surface unit of the expanded stent. In fact the surface covered with metal must never exceed 14÷15% of the total surface.

It is clear that variants and/or additions can be foreseen for what has been described and illustrated above.

The slot 114 can have any form other than that shown in the figures. Moreover, the slot 114 could be foreseen in a different coil from that of the end, or on another loop.

The number of the bridges 12, the coils 11, the arms 110 and the loops 111 can vary in relation to what has been described and illustrated above. The form of the coils 11 can also vary.

In general, all the above described characteristics in relation to possible specific embodiments can be realised independently from each other.

In order to satisfy specific and contingent requirements, those skilled in the art will be able to make numerous modifications, adaptations, and replacement of elements with others that are functionally equivalent to the above described preferred embodiments of the endolumenal stent, while remaining within the context of the following claims.

What is claimed is:

1. An endolumenal prosthesis, comprising a tubular body adapted to convert from a contracted condition to an expanded condition, said tubular body being developed along a longitudinal axis, said tubular body comprising:
a plurality of coils made of a non-bioabsorbable material that develop in a substantially circumferential direction, and
at least two bridges connecting two coils of the plurality of coils, the two coils being adjacent to each other along the longitudinal axis, said at least two bridges comprising:
at least one bioabsorbable bridge connecting the two coils and made of a bioabsorbable material; and
at least one non-bioabsorbable bridge connecting the two coils and made of the non-bioabsorbable material, wherein said at least one non-bioabsorbable bridge and said at least one bioabsorbable bridge are spaced apart from each other along said substantially circumferential direction between the two coils.

2. An endolumenal prosthesis according to claim 1 wherein said endolumenal prosthesis is of the self-expandable type.

3. An endolumenal prosthesis according to claim 2 wherein at least one coil is made of superelastic material or in hardened pseudoelastic material.

4. An endolumenal prosthesis according to claim 2 wherein at least one coil is made of shape memory material.

5. An endolumenal prosthesis according to claim 4, wherein said shape memory material is NiTinol.

6. An endolumenal prosthesis according to claim 1 wherein said endolumenal prosthesis is of the balloon-expandable type.

7. An endolumenal prosthesis according to claim 6 wherein at least one coil is made of stainless steel.

8. An endolumenal prosthesis according to claim 7, wherein said stainless steel is of the type classified as AISI 316 L.

9. An endolumenal prosthesis according to claim 6 wherein at least one coil is made of Chromium-Cobalt alloy.

10. An endolumenal prosthesis according to claim 9, wherein said Chromium-Cobalt alloy is of the type classified as UNS R30035.

11. An endolumenal prosthesis according to claim 1 wherein said coils define closed courses.

12. An endolumenal prosthesis according to claim 1 wherein said coils develop according to said substantially circumferential direction.

13. An endolumenal prosthesis according to claim 1 wherein each bridge of said at least two bridges has a substantially straight line development and an extension oriented in an approximately axial direction.

14. An endolumenal prosthesis according to claim 1 wherein said at least two bridges develop in said substantially circumferential direction.

15. An endolumenal prosthesis according to claim 14, wherein said at least two bridges form a pseudo-coil.

16. An endolumenal prosthesis according to claim 1 wherein each bridge of said at least two bridges has a slightly sloping direction in relation to the axial direction.

17. An endolumenal prosthesis according to claim 1 wherein all of said at least two bridges included between two coils are parallel with each other.

18. An endolumenal prosthesis according to claim 1 wherein each bridge of said at least two bridges alternates in directions having opposite slopes in relation to the longitudinal axis direction.

19. An endolumenal prosthesis according to claim 1 wherein at least one of said coils comprises fixation actuators in a point wherein a bridge branches off.

20. An endolumenal prosthesis according to claim 19, wherein said fixation actuators comprise a hole made in the width of the coil.

21. An endolumenal prosthesis according to claim 20, wherein said bridge comprises a profile that locally replicates with great precision the contour of the profile of the coil and portions which are complementary to said fixation actuators, adapted to provide shape coupling between the coil and the respective bridge.

22. An endolumenal prosthesis according to claim 19, wherein said fixation actuators comprise shaped protrusions positioned externally on the width of the coil.

23. An endolumenal prosthesis according to claim 19, wherein said fixation actuators comprise an incised line on the surface of the coil.

24. An endolumenal prosthesis according to claim 19, wherein said fixation actuators comprise a highly porous level on the surface of the coil.

25. An endolumenal prosthesis according to claim 1, wherein said at least one bioabsorbable bridge is made of a bioabsorbable polymer.

26. An endolumenal prosthesis according to claim 25, wherein said bioabsorbable polymer is selected from the group composed of PDLA or poly-(D-lactic acid), PLLA or poly-(L-lactic acid), and PGA or poly-(glycolic acid).

27. An endolumenal prosthesis according to claim 25 wherein said bioabsorbable polymer is selected from the group composed of: poly-caprolactone, poly-(lactide-co-glycolide), poly-(ethylene-vinyl acetate), poly-(hydroxybutyrate-co-valerate), poly-dioxanone, poly-orthoester, poly-anhydride, poly-(glycolic acid-co-trimethylene carbonate), poly-phosphoester, poly-phosphoester urethane, poly(amino acids), cyanoacrylates, poly-(trimethylene carbonate), poly-(iminocarbonate), copoly-(ether-esters) (PEO/PLA), poly-alkylene oxalates, poly-phosphazenes and biomolecules such as fibrin, fibrinogen, cellulose, starch, collagen, hyaluronic acid, poly-N-alkylacrylamides, poly-depsi-peptide carbonate, and poly-ethylene-oxide based polyesters.

28. An endolumenal prosthesis according to claim 1, wherein said at least one bioabsorbable bridge is made of a bioabsorbable metallic material.

29. An endolumenal prosthesis according to claim 1, wherein at least one bioabsorbable bridge is made of a Magnesium alloy.

30. An endolumenal prosthesis according to claim 29, wherein said Magnesium alloy is of the type classified as UNS M18430.

31. An endolumenal prosthesis according to claim 1, wherein said at least one bioabsorbable bridge is made of a binary mixture Calcium oxide (CaO) and Phosphorous pentoxide (or Phosphoric anhydride)($P_2O_5$).

32. An endolumenal prosthesis according to claim 1, wherein each bridge of said at least two bridges forms a loop adapted to enclose a loop of a coil in order to form a chain connection.

33. An endolumenal prosthesis according to claim 32 wherein each of the beams comprises at its distal end, a keel.

34. An endolumenal prosthesis according to claim 33 wherein, when the endolumenal prosthesis is in its contracted condition, and the beams are in contact with one another, the plurality of keels creates a tip.

35. An endolumenal prosthesis according to claim 1, wherein each bridge of said at least two bridges assumes the form of a beam having a mainly axial development and connected to more than two coils.

36. An endolumenal prosthesis according to claim 35 wherein said beam is positioned inside said coils and is connected to their radially internal surface.

37. An endolumenal prosthesis according to claim 36 wherein said radially internal surface of said coils comprises fixation actuators adapted to form a shape coupling with said beam.

38. An endolumenal prosthesis according to claim 35 wherein said endolumenal prosthesis comprises a plurality of beams which, when the endolumenal prosthesis is in its contracted condition, enter into contact with each other, thus forming a tubular structure positioned inside the coils.

39. An endolumenal prosthesis according to claim 38 wherein said tubular structure defines, at its distal end, an opening adapted to receive a guidewire.

40. Device for the transport and delivery of an endolumenal prosthesis according to claim 38, comprising a catheter and a sheath adapted to supply a radial containing system for the endolumenal prosthesis, wherein
said catheter comprises, at its distal end, a shoulder adapted to provide an axial support for the tubular structure of the endolumenal prosthesis; and
the length of said sheath extends further than that of said catheter by a length substantially equal to that of the endolumenal prosthesis.

41. An endolumenal prosthesis according to claim 1, wherein at least one coil comprises a marker made of radiopaque material.

42. An endolumenal prosthesis according to claim 1, wherein the coils positioned at the distal end and proximal end respectively, comprise a marker made of radiopaque material.

43. An endolumenal prosthesis according to claim 1, wherein the parts made of bioabsorbable material are adapted to release a drug in a controlled manner over a prolonged period of time.

44. An endolumenal prosthesis according to claim 1, wherein each single loop of each single coil is connected by a bridge to the respective loop of the adjacent coil.

45. An endolumenal prosthesis according to claim 1, wherein said non-bioabsorbable material comprises a metallic material.

46. An endolumenal prosthesis according to claim 1, wherein said non-bioabsorbable material comprises a material selected from the group consisting of superelastic material, Nitinol, stainless steel, and Chromium-Cobalt alloy.

* * * * *